(12) United States Patent
Mizuno et al.

(10) Patent No.: US 6,949,252 B2
(45) Date of Patent: Sep. 27, 2005

(54) METHOD FOR PREPARING AN IMPLANTABLE MULTILAYER TISSUE CONSTRUCT

(75) Inventors: Shuichi Mizuno, Brookline, MA (US); Toshimasa Tokuno, Tokyo (JP); Laurence J. Berlowitz Tarrant, Easthampton, MA (US)

(73) Assignee: Histogenics, Corp., Northhampton, MA (US)

( * ) Notice: Subject to any disclaimer, the term of this patent is extended or adjusted under 35 U.S.C. 154(b) by 263 days.

(21) Appl. No.: 10/104,677

(22) Filed: Mar. 22, 2002

(65) Prior Publication Data

US 2003/0040113 A1 Feb. 27, 2003

Related U.S. Application Data

(60) Provisional application No. 60/352,085, filed on Jan. 24, 2002, and provisional application No. 60/278,534, filed on Mar. 23, 2001.

(51) Int. Cl.$^7$ .......................... A61F 2/00; C12N 11/02; C12N 11/08; C12N 5/06; C12N 5/08
(52) U.S. Cl. ..................... 424/423; 424/93.7; 435/177; 435/180; 435/395
(58) Field of Search .................. 424/423, 426, 424/93.7; 435/174, 177, 178, 180, 395

(56) References Cited

U.S. PATENT DOCUMENTS

| | | | |
|---|---|---|---|
| 4,522,753 A | | 6/1985 | Yannas et al. ........... 260/123.7 |
| 4,851,354 A | * | 7/1989 | Winston et al. ............. 435/402 |
| 5,206,028 A | | 4/1993 | Li et al. ...................... 424/484 |
| 5,656,492 A | | 8/1997 | Glowacki et al. ......... 435/284.1 |
| 5,902,741 A | | 5/1999 | Purchio et al. ......... 435/240.23 |
| 5,928,945 A | | 7/1999 | Seliktar et al. ............. 435/395 |
| 6,080,194 A | | 6/2000 | Pachence et al. ............. 623/18 |
| 6,171,610 B1 | | 1/2001 | Vacanti et al. .............. 424/426 |
| 6,312,725 B1 | * | 11/2001 | Wallace et al. ............. 424/484 |
| 6,432,713 B2 | * | 8/2002 | Takagi et al. ................ 435/395 |

FOREIGN PATENT DOCUMENTS

| | | | |
|---|---|---|---|
| JP | 622744 | 2/1994 | |
| WO | WO9844874 | 10/1998 | ............. A61F/2/08 |

OTHER PUBLICATIONS

Richard W. Farndale, et al., A Direct Spectrophotometric Microassay For Sulfated Glycosaminoglycans In Cartilage Cultures, *Connective Tissue Research*, 9:247–248 (1982).

* cited by examiner

*Primary Examiner*—David M. Naff
(74) *Attorney, Agent, or Firm*—Hana Verny (57) ABSTRACT

The present invention relates to compositions and methods for preparing tissues or tissue constructs. In selected embodiments, the invention relates to the construction of a multi-layered biological structure (i.e. system) that includes a cellular support matrix seeded with living cells derived from a native tissue. The present invention also relates to tissue culture protocols to promote the in vitro growth of tissues and tissue constructs.

16 Claims, 6 Drawing Sheets

METHOD FOR PREPARING AN IMPLANTABLE MULTILAYER TISSUE CONSTRUCT

This application claims benefit of provisional applications 60/278,534, filed Mar. 23, 2001, and 60/352,085, filed Jan. 24, 2002.

FIELD OF THE INVENTION

The present invention relates to compositions and methods for preparing tissues and tissue constructs. In particular, the invention recites compositions and methods which incorporate cells into biological matrices.

BACKGROUND

Vertebrate tissues and organs often fail to recover normal form and function when damaged and often fail (due to metabolic and/or mechanical trauma) to adequately integrate with a host when transplanted. In attempts to reconstruct tissues and organs; surgeons have implanted either living tissues or non-living materials in place of damaged or resected native anatomical structures. These traditional techniques have limitations. For example while autografts are histocompatible, the loss of tissue from the donor site often creates anatomical and/or physiological pathologies in the very same host. On the other hand, transplanted allografts and xenografts often provoke a pathological immune response which is proximal to the rejection of these grafts by the host.

Non-living transplant materials are of marginal utility in the repair and transplant of native tissues, tissue constructs, and organs. Specifically, transplanted non-living materials are especially subject to extrusion, infection, and scar tissue formation.

The use of bioengineered tissue as alternatives to transplanted native tissues and non-living materials has also been described. For example, U.S. Pat. No. 5,902,741 to Purchio et al. teaches a method for culturing cartilage tissue in vitro using a framework inoculated with a nutrient medium bearing cartilage cells or precursors. Similarly, U.S. Pat. No. 5,928,945 to Selektar et al. teaches a process for producing bioengineered neo-cartilage by applying fluid-flow shear flow stress to chondrocytes. In another example U.S. Pat. No. 6,080,194 to Pachence et al teaches a template for producing articular cartilage comprising a dense collagen matrix placed on the surface of the cartilage defect to prevent cell migration and vascular in-growth from the sub-chondral plate.

However, these compositions and methods (in the prior art) only approximate a fraction of the anatomical and physiological repertoire of the native tissue they are attempting to replace. More specifically, these shortcomings in the prior art may, in part, be attributed to the inability to uniformly seed, culture, and differentiate cells across the entire cross section of a three-dimensional cellular support layer. What is needed, therefore, are transplantable tissue and tissue constructs that can support cells in their normal metabolic state and can anatomically and physiologically integrate with a host without provoking a pathogenesis.

SUMMARY OF THE INVENTION

The present invention relates to compositions and methods for the preparation of tissues and tissue constructs. In selected embodiments, the invention relates to the construction of a multi-layered biological structure (i.e. system framework) comprising living cells incorporated into a cellular support matrix.

In one embodiment the present invention contemplates a composition comprising a first integration layer; a second cellular support layer (comprising a matrix) operably linked to said first integration layer wherein said support layer is seeded with cells (suspended in a gel), and a third protective layer operably linked to said first and second layers.

It is not intended that the present invention be limited to a composition comprising a multi-layered system have a specific number of layers. In one embodiment, said multi-layered system comprises two layers. In a preferred embodiment, said multi-layered system comprises three layers. In another embodiment, said multi-layered system comprises more than three layers.

It is not intended that the present invention be limited to a specific method for constructing a cellular support matrix. Japanese Patent No. 6,022,744 (herein incorporated by reference) entitled, "Collagen Carrier For Cell Culture" describes the preparation of a matrix suitable for use a cellular support layer described in the present invention.

It is not intended that the gel element of said cell support layer be limited to a single composition. In one embodiment, said gel element comprises gelatin. In another embodiment, said gel element comprises collagen. In a preferred embodiment, said gel element comprises Type I collagen.

It is not intended that the compositions and methods of the present invention be limited to cells harvested from any particular species. In one embodiment, said cells are mammalian cells. In a preferred embodiment, said cells are from a human.

In one embodiment the cells used in the composition and methods of the present invention are cells are harvested from epithelial tissue, connective tissue, muscular tissue and/or nervous tissue. In one embodiment said cells are osteocytes. In another embodiment said cells are ligament fibroblasts. In another embodiment said cells are tenocytes. In another embodiment said cells are synovial fibroblasts. In a preferred embodiment, said cell are chondrocytes harvested from connective tissue. In a preferred embodiment, said connective tissue is cartilage.

In one embodiment, the present invention describes methods for preparing tissues or tissue constructs using a multi-layered system that includes a cellular support matrix seeded with living cells directly isolated and/or expanded from viable tissue. In a preferred embodiment, the present invention contemplates a method providing a cellular support matrix, a gel, and cells; mixing said cells with said gel to form a cell suspension; and contacting said cell suspension with said cellular support matrix to create a cell seeded matrix.

In another embodiment, the present invention further comprises applying heat to said cell-seeded matrix under conditions that said gel is cured into a substantially solid form, thereby, forming a heat cured cell-seeded matrix.

In another embodiment, the present invention further comprises culturing said heat-cured cell-seeded matrix under conditions comprising constant or cyclic hydrostatic pressure, wherein said cellular support matrix consists essentially of porous Type I collagen and said cells are chondrocytes.

In one embodiment, the present invention describes a method, comprising: a) providing, i) a solution comprising suspended chondrocytes; ii) a sponge matrix; and iii) a treatment means; b) introducing said sponge matrix into said solution under conditions such that said solution enters said sponge by capillary action and said chondrocytes contact said matrix so as to create a seeded device; and c) treating said seeded device with said treatment means under conditions such that at least a portion of said solution solidifies within said device.

In one embodiment of the present invention, said treatment means comprises a culture chamber. In another embodiment, the present invention contemplates a treatment, of said seeded device, comprising heating in the absence of carbon dioxide.

In one embodiment of the present invention, the sponge matrix is configured to be transplanted into a joint of a human being.

In one embodiment of the present invention, the chondrocyte suspension solution comprises neutralized aqueous Type I collagen.

In another embodiment the present invention further comprises, after step (c) above, culturing said chondrocytes under conditions such that said chondrocytes elaborate gene products associated with the extracellular matrix. In one embodiment said culturing is performed under pressure greater than 1 atmosphere of pressure. In another embodiment, said culturing is performed under constant or cyclic hydrostatic pressure wherein said cyclic hydrostatic pressure is in a range of approximately 0.01–10.0 MPa at 0.5 Hz. In another embodiment, said cyclic hydrostatic pressure is in a range of 0.5–5.0 MPa at 0.5 Hz. In a preferred embodiment, said cyclic hydrostatic pressure is approximately 3.0 MPa of pressure at 0.5 Hz. In one embodiment the duration of said cyclic pressure is 1–30 days. In another embodiment, the duration of said cyclic pressure is 5–8 days. In a preferred embodiment, the duration of said cyclic pressure is approximately 6 days.

In one embodiment the present invention contemplates a resting phase (following exposure to cyclic pressure). In one embodiment, the duration of said resting phase is in the range of 1–60 days. In one embodiment, the duration of said resting phase is in the range of 4–21 days. In a preferred embodiment, said resting phase is approximately 12 days.

In another embodiment the present invention describes a method, comprising: a) providing i) a solution comprising chondrocytes suspended in aqueous collagen; ii) a cellular support matrix; and iii) a treatment means; b) introducing said matrix into said solution under conditions such that said solution enters said sponge by capillary action and said chondrocytes contact said matrix so as to create a seeded device; and c) reacting said seeded device with said treatment means under conditions such that at least a portion of said solution solidifies within said device.

In one embodiment of the present invention, said chondrocytes suspension solution is at least partially gelled.

In one embodiment of the present invention, the treatment means comprises a culture chamber. In another embodiment the treatment comprises heating in the absence of carbon dioxide.

In one embodiment of the present invention the sponge matrix comprises Type I collagen configured to be transplanted into a joint of a human being.

In another embodiment, the present invention further comprises, after step (c), culturing said chondrocytes under conditions such that said chondrocytes elaborate gene products associated with the extracellular matrix.

In one embodiment of the present invention, said culturing is performed under pressure of 1 atmosphere or greater.

In another embodiment, said culturing is performed under constant or cyclic hydrostatic pressure wherein said cyclic hydrostatic pressure is in a range of approximately 0.01–10.0 MPa at 0.5 Hz. In another embodiment, said cyclic hydrostatic pressure is in a range of 0.5–5.0 MPa at 0.5 Hz. In a preferred embodiment, said cyclic hydrostatic pressure is approximately 3.0 MPa of pressure at 0.5 Hz. In one embodiment the duration of said cyclic pressure is 1–30 days. In another embodiment, the duration of said cyclic pressure is 5–8 days. In a preferred embodiment, the duration of said cyclic pressure is approximately 6 days.

In one embodiment the present invention contemplates a resting phase (following exposure to cyclic pressure). In one embodiment, the duration of said resting phase is in the range of 1–60 days. In another embodiment, the duration of said resting phase is in the range of 4–21 days. In a preferred embodiment, said resting phase is approximately 12 days.

It is not intended that the present invention be limited to a situation wherein said chondrocytes suspended in a sol-gel solution. It is not intended that the present invention be limited to any specific degree of gellation for said chondrocyte containing sol-gel solution.

It is not intended that the present invention be limited to a situation wherein the entire chondrocytes suspension solution solidifies. That is to say, it is sufficient that a significant portion of the solution solidifies, thereby in one embodiment, substantially immobilizing the suspended cells within a seeded matrix.

In one embodiment, the present invention contemplates a system, comprising: i) a cellular support layer configured to permit growth of cells in three-dimensions, said cellular support layer having an integrative side and a functional side, and wherein said cellular support is seeded with at least one cell type to create seeded cells; ii) an integration layer contacting said integrative side of said cellular support layer, wherein said integration layer is configured to be insertable into tissue; and iii) a protective layer contacting said functional side of said cellular support layer, said protective layer configured to protect said seeded cells from the effects of blood-borne agents.

In one embodiment of the present invention, said blood-borne agents are clotting factors, cytokines, and/or cytotoxic cells. In one embodiment of the present invention, said seeded cells are in contact with a nutrient fluid. In another embodiment of the present invention, said integration layer is configured to be insertable into tissue following surgery.

In one embodiment of the present invention contemplates a method for inserting a system comprising: i) a cellular support layer configured to permit growth of cells in three-dimensions, said cellular support layer having an integrative side and a functional side, and wherein said cellular support is seeded with at least one cell type to create seeded cells; ii) an integration layer contacting said integrative side of said cellular support layer, wherein said integration layer is configured to be insertable into tissue; and iii) a protective layer contacting said functional side of said cellular support layer, said protective layer configured to protect said seeded cells from the effects of blood-borne agents and into the tissues of a patient. In another embodiment, the insertion of the system into the patient follows surgery on said patient.

DEFINITIONS

As used herein, the term "tissue" refers to a collection of similar cells and the intercellular substances surrounding them. It will be appreciated by those of ordinary skill in the art that there are four basic tissue types in the body, 1) epithelium; 2) connective tissue including blood, bone and cartilage; 3) muscle; and 4) nerve.

As used herein, the term "neo-tissue" refers to a composition, comprising cells, that approximates the form and function of a native tissue in situ.

As used herein, the term "neo-organ" refers to a synthetic composition, comprising cells, that approximates the form and function of a native organ in situ.

As used herein, the term "neo-cartilage" refers to a plurality of chondrocytes in a transitional state of histogenesis. This transitional state of histogenesis is characterized by the elaboration of gene products associated with the extracellular matrix (i.e. GAG's) and a morphology comprising partial encapsulation into lacunae. In one embodiment, this neo-cartilage is manufactured by Histogenics Corporation (Easthampton, Mass.) under the trademark NEOCART.

As used herein, the term "tissue construct" refers to a substantially avascular mixed population of cells that (in a preferred embodiment) is propagated in a tissue culture system including, but not limited to, the TESS tissue processor.

The term "neo-tissue construct" refer to tissue constructs formed de novo from cells or tissue by the methods of the present invention.

As used herein, the term "native environment" refers to the in situ biological environment supporting a native tissue or a tissue construct.

As used herein, the term "biocompatible" refers to compositions (e.g. cells, tissues, matrices, etc.) that do not substantially disrupt the normal biological functions of other compositions to which they contact. For example, the present invention contemplates a composition comprising a multi-layered system having a physical and chemical structure which is biocompatible with the cells and tissue produced by said system (e.g. neo-tissues), and which is also biocompatible with the cells or tissues into which said system (and its cells or tissue) is delivered. In selected embodiments, the present invention also contemplates biocompatible materials that are both biodegradable and non-biodegradable.

As used herein, the term "matrix" refers to a composition comprising a plurality of pores dividing free space into partially enclosed interstices wherein said interstices are in fluidic communication. One type of matrix is a "sponge matrix" comprising a matrix that takes up fluid by capillary action. In selected embodiments, the present invention contemplates a composition comprising a cellular support layer, wherein said cellular support layer comprises a collagenous sponge matrix.

As used herein, the term "TESS matrix" refers to a commercial (a proprietary composition manufactured by Koken Company LTD., Toyko Japan) embodiment of the cellular support layer described in the present invention.

As used herein, the term "pore size" refers to the average cross-sectional dimension of interstices in a matrix.

As used herein, the term "functional surface," refers to the surface that is directed toward a region of a cell, tissue or organ carrying out at least one function. For example, in a system for producing cartilage, the term "functional surface" refers to the surface facing the synovium when the system is implanted in a host. Likewise, in a system for producing oral mucosa, the term "functional surface" refers to the surface facing the inside of the mouth once the system is implanted into a host.

As used herein, the term "donor" refers to a human or non-human from whom cells, tissues, blood, or an organ is taken for transplantation.

As used herein, a "host" refers to an individual (whether human or non-human) into whom cells, tissue, blood, or organs are transplanted. For example, the present invention contemplates methods in which cells (e.g. chondrocytes) are taken from a donor for multiplication in vitro and transplantation into a host (whether the donor and host are the same individual, or different individuals).

As used herein, the word "chondrocyte" refers to a specific type of cartilage cell. In vivo, these cells are characterized by distinct morphologies and physiologies (observed in situ) as compared to the in vitro morphologies and physiologies (as observed in tissue culture) for these same cells. For example, chondrocytes harvested from adult mammalian trochlea are substantially non-dividing and elaborate substantially no extracellular matrix (i.e. GAG's). In contrast substantially quiescent chondrocytes isolated from adult mammalian trochlea are activated in vitro (for example when placed in tissue culture) such that a majority of these cultured cell divide and produce, in vitro, gene products associated with the extracellular matrix (i.e. GAG's).

As used herein, the term "suspended chondrocytes" refers to any number of chondrocytes in a fluid. In a preferred embodiment said fluid comprises aqueous Type I collagen.

As used herein, the term "delivering tissue" refers to the process of introducing, inserting, injecting or transplanting cells or tissue from a donor into a host. For example, the present invention contemplates methods wherein tissue grown in the multi-layered system of the present invention (i.e. neo-tissue) is delivered into a host at, for example, the site of a lesion (i.e. target lesion).

As used herein, the term "cyclic hydrostatic pressure" (and the abbreviation "CHP") refers to the application of repeated (e.g. two or more) periods of applied hydrostatic pressure (within a defined loading interval) which preferably create a sine wave form of measured pressure. In a preferred embodiment said CHP is 3.0 MPa at 0.5 Hz.

As used herein, the term "constant pressure" refers to the application of a substantially non-fluctuating (e.g. plus or minus 20% or less, or more preferably 5% or less) or non-cyclic pressure load over a period of time.

As used herein, the term "loading" or "loading interval" refers to a period of applied CHP load followed by a return to ambient pressure (e.g. wherein no external pressure is applied).

As used herein, the term "resting phase" refers to a variable length of time wherein cells are maintained in culture at approximately atmospheric pressure after exposure to or culturing under cyclic hydrostatic pressure.

As used herein, the term "de novo formation" refers to the production of cells (e.g. chondrocytes, fibroblasts, fibrochondrocytes, tenocytes and osteoblasts) or tissues (e.g. cartilage connective tissue, fibrocartilage, tendon, and bone) within a support structure (e.g. multi-layered system, scaffold or collagen matrix.

As used herein the term, "Type I collagen" is characterized by two alpha 1(I) chains, and one alpha2(I) chains (heterotrimeric collagen). The alpha1 (I) chains are approximately 300 nm long. Type I collagen is predominantly found in bone, skin (in sheet-like structures), and tendon (in rope-like structures). Type I collagen is further typified by its reaction with the protein core of another connective tissue component known as a proteoglycan.

As used herein, the term "Type II collagen" collagen is characterized by three identical alpha1(II) chains (homotrimeric collagen) present on chromosome 12. Type II collagen in cartilage presents as thin fibrils in a lose mesh, strongly interacting with other components (especially proteoglycans). Type II collagen is covalently cross-linked to type IX collagen and other FACIT collagens, that help in the formation of type II collagen. This molecule is also able to bind and interact with integrin and decorin molecules.

As used herein, "neutralized aqueous Type I collagen" refers to Type I collagen without charge.

As used herein, "MMP" refers to "matrix metalloproteinase". MMP associated with cartilage degeneration in a diseased joint. MMP may be further distinguished as MMP-1, MMP-2, MMP-9, etc.

As used herein, the term "MPa" means MegaPascal. One MPa is equal to 145 psi.

As used herein, the term "mandrel" refers to a tapered or cylindrical axle, spindle, or arbor that serves as a core around which material may be cast molded, forged, bent, or otherwise shaped.

As used herein, the term "epithelial tissue" refers to the cellular (typically avascular) layer covering all the free surfaces, cutaneous, mucous, and serous, including the glands and other structures derived there from. Epithelial tissue present squamous, cuboidal, and/or columnar cells upon histological examination. In addition, epithelial tissue may be described as simple, stratified or pseudostratified.

As used herein, the term "connective tissue" refers to tissue that protects and supports the body and its organs, and tissues that bind organs together. Examples of such tissues include (but are not limited to) mesenchyme, mucous connective, areolar (loose), adipose, reticular, elastic, collagenous, bone, blood, or cartilage tissue (e.g. hyaline, fibro, and elastic cartilage).

As used herein, the term "muscular tissue" refers to tissue that is characterized by the ability to contract upon stimulation and may be categorized as skeletal, cardiac, and smooth.

As used herein, the term "nervous tissue" refers to tissue (comprising nerve fibers, dendrites, and supporting tissues) that initiate and transmit nerve impulses.

As used herein, the terms "membrane tissue" and "membranous tissue" refer to a combination of epithelial tissue and connective tissue that forms a membrane. Examples of such membranes include (but are not limited to) mucous, serous, cutaneous, and synovial membranes.

As used herein the term, "sol-gel solution" refers to a colloidal suspension which may transition from a liquid (sol) to a more solid material (gel). In a preferred embodiment, the "sol" is a suspension of aqueous collagen that is transitioned, by heat treatment, into a gel.

As used herein, the term "gel" or "gelled" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.).

As used herein, the term "partially gelled" refers to the state of matter between liquid and solid such that a substance demonstrates more of the properties of a liquid (i.e., the shape is resilient and deformable) and fewer of the properties of a solid (i.e., the shape is discrete enough to maintain three dimensions on a two dimensional surface.).

As used herein the term "solidifies" or "solidified" refers to any process by which a substance is made solid, compact, or hard.

As used herein the term "partially solidifies" or "partially solidified" refers to any process by which a substance is made to some degree more solid, compact, or hard as compared to the substance acted on.

As used herein, the words "cure" or "cured" refers the application of a chemical or physical process to further solidify a gel.

As used herein, the term "treatment means" refers to any device that can regulate temperature, atmospheric pressure, and/or gas saturation.

As used herein, the term "seeded device" refers to a matrix containing any number of cells. In a preferred embodiment, said seeded device comprises chondrocytes disposed within a collagenous sponge matrix.

As used herein, the term "elaborate gene products" refers to the production of peptides and/or proteins by a cells. In a preferred embodiment, chondrocytes produce proteins associated with the extracellular matrix of cartilage (including but not limited to GAGs).

DETAILED DESCRIPTION OF THE INVENTION

The present invention relates to compositions and methods for the preparation of neo-tissues and tissue constructs. In preferred embodiments, the invention relates to the construction of a multi-layered biological structure (e.g. any three dimensional form) that includes at least one matrix layer seeded with living cells.

I. General Design of a System for the Production of Tissues and Tissue Constructs The present invention provides a composition comprising a matrix which contains cells, originally harvested from an in situ organ or tissue, that have been subsequently expanded (via cell culture in vitro) prior to seeding within said matrix. In one embodiment this composition, comprising a seeded matrix, is placed (like a cassette) into a tissue culture apparatus (in one example a tissue processor) such that the cells disposed within said system may expand in number and/or differentiate. It is not intended that the present invention be limited to any specific type of cell. In a preferred embodiment, said cells are chondrocytes which multiply and differentiate when cultured under conditions including cyclic hydrostatic pressure.

The present invention is not limited to a specific configuration. In one embodiment, however, the present invention is a system comprising two layers.

The cellular support layer provides a platform which contains the cells seeded into the system and provides support for said cells as they: a) divide and differentiate (in a tissue culture apparatus) into a neo-tissue and b) when said system is implanted into a host.

The integration layer protects the neo-tissue as it divides, ex vivo, in a tissue culture apparatus. Once said neo-tissue is implanted into a host, the integration layer is oriented to oppose a native tissue surface of said host, thereby, exposing said neo-tissue to the milieu, including humoral factors (e.g. hormones and trophic factors), at the transplant site.

In some embodiments, the system also comprises a protective layer which substantially encapsulates the cellular support layer and the integration layer. The systems multi-layered design may be fabricated into a variety of forms. In one embodiment, the system may be a sheet. In another embodiment, the system can be formed to approximate the three-dimensional structure of a tissue or organ as observed in vivo including, but not limited to tubes, ellipsoids, and claviforms.

The neo-tissues (or "products") propagated according to the methods recited in the present invention substantially replicate native tissues. Specifically, the systems and methods of the present invention produce tissues that substantially reproduce the anatomy and physiology of native tissues. In one embodiment, the neo-tissues recited in the present invention are propagated from cell originally harvested from intended host (e.g. are autologous). In some embodiments the integration and cellular support layers of the present invention are biodegradable. In these embodiments, the non-cellular components of the system biodegrade such that, after implantation into a host, only the neo-tissue is integrated into the host.

As described above the multi-layered system comprises at least two layers, a cellular support layer and an integration layer. In selected embodiments, the system also incorporates a protective layer. Each of these layers is described more fully below. However, the present invention also contemplates the incorporation supplementary layers into the system. These supplementary layers may contain a variety of trophic factors including, but not limited to, epidermal growth factor (EGF), transforming growth factor β (e.g. TGF β-1, TGF β-2, etc.), platelet derived growth factor (e.g. PDGF-AA, PDGF-AB and PDGF-BB), fibroblast growth factors (FGF), insulin-like growth factors (IGF), tumor necrosis factors (TNF), colony stimulating factors (CSFs), nerve growth factors (NGF), connective tissue growth factor (CTGF), brain-derived neurotropic factor (BDNF), ciliary neurotrophic factor (CNTF), pro-angiogenic or anti-angiogenic factors, and other therapeutic agents including, but not limited to, cytokines, interleukins (e.g. IL-1, IL-2) or other co-factors such as heparin or calmodulin, antibiotics, anti-neoplastic agents, and anti-bacterials, to further stimulate or control tissue remodeling, or to control sepsis.

In other embodiments, such supplementary layers may provide ontogenic or morphogenic factors such as, bone morphogenic proteins (BMP 1–8); hedgehog (hh) family gene products; Hox family gene products; Pax family gene products; Notch gene products; osteoprotegerin; and osteoprotegerin binding proteins. It is important to note that although the general design of the system of the present invention provides for a system comprising more than one layer, the present invention also contemplates embodiments comprising only the cellular support layer.

II. The Components of the Multi-Layered System

1. The Cellular Support Layer (and "TESS Matrix")

The cellular support layer of the present invention (in a specific commercial embodiment referred to as the "TESS matrix") comprises a matrix that facilitates the three-dimensional propagation of tissue and tissue constructs. The function of the cellular support layer is, in part, to provide a growth platform for cells (in one example chondrocytes). Desirable features of the cellular support layer include (but are not limited to) biocompatibility, hydrophilicity, and neutral charge. In one embodiment, the cellular support layer comprises a matrix (or honeycomb-like lattice) fabricated substantially from Type I collagen. In one preferred embodiment said honeycomb-like Type I collagen matrix is referred to as the "TESS matrix".

It is not intended that this cellular support layer be limited to any specific material or formulation. For example, the matrix described in Japanese Patent No. 6,022,744 is suitable for use as a cellular support layer as described in the present invention. This matrix is prepared by gelling an acidic aqueous collagen solution with ammonia gas to form a collagen gel and then freeze drying said gel to evaporate substantially all to the water, thereby, forming a substantially porous dried matrix.

In one example, 300 grams of a 1% aqueous atelocollagen solution (maintained at pH 3.0) is poured into a 10×20 cm tray. This tray is then placed in a 5 liter container. A 50 ml open container containing 30 ml of a 3% aqueous ammonia solution is then placed next to the tray, in the 5 liter chamber, containing 300 grams of said 1% aqueous solution of atelocollagen. The 5 liter container (containing the open trays of atelocollagen and ammonia) is then sealed and left to stand at room temperature for 12 hours. During this period the ammonia gas released from the open container of aqueous ammonia, and confined within the sealed 5 liter container, is reacted with the aqueous atelocollagen, thereby, gelling said aqueous solution of atelocollagen.

This collagenous gel is then washed with water overnight and, subsequently, freeze-dried to yield a sponge like matrix. This freeze dried matrix is then cut into squares, sterilized, and stored under a sterile wrap.

The present invention contemplates matrices prepared according to other protocols. In one embodiment, the matrix prepared according to the protocol set out in U.S. Pat. No. 5,206,028 to Li (herein incorporated by reference) will be used. In another embodiment, the collagen matrices prepared according to the protocols set out in U.S. Pat. No. 5,656,492 to Glowacki et al. (herein incorporated by reference) will be used.

The pore size of these collagen matrices may be adjusted by varying the dispersion pH, collagen concentration and the lyophilization cycle (e.g. freezing time, temperature range and cycle time). See, U.S. Pat. No. 4,522,753 to Yannas et al., herein incorporated by reference. While it is not intended that the present invention be limited to any specific mechanism, adjustment to pore size can be advantageous in promoting the even distribution of cells with different morphologies.

For example, chondrocytes cultured in a Type I collagen matrix show increased infiltration into said matrix when the average pore size of said matrix was greater than 100 micrometers. See, U.S. Pat. No. 6,080,194 to Pachence et al, herein incorporated by reference. While it is not intended that the support layer of the present invention be limited to a specific pore size, in one embodiment of the present invention said pore size is in a range of approximately 50–500 micrometers. In another embodiment, the pore size is in a range of 100–300 micrometers. In another embodiment the pore size is approximately 200 micrometers.

It is not intended that the present invention be limited to a cellular support layer comprising Type I collagen. In other embodiments, the cellular support layers of the system are composed of other materials, including (but not limited to): other collagens such as Type II and Type IV collagens; cell-contracted collagen gels containing other components of the extra-cellular matrix such as proteoglycans, glycosaminoglycans, glycoproteins (e.g. fibronectin, laminin, etc.); elastin and/or bioactive peptide growth factors or cytokines; other biopolymers such as fibrin; synthetic biodegradable fibers made from such polymers as polylactic or polyglycolic acids, polycaprolactones, or polyamino acids, or their copolymers; and construct structures comprising collagen and polylactic acid.

2. Gel Component

In a preferred embodiment of the present invention, the cellular support matrix of the present invention acts like a sponge that wicks up (and evenly distributes throughout the interstices of the matrix) cells suspended in a sol-gel solution wherein said sol-gel solution is in its sol state. It is not intended that the present invention be limited to a specific type of sol-gel. However, preferred characteristics of this sol-gel include, but are not limited to, a viscosity (as a sol) that promotes easy mixing of cells under conditions such that only nominal shear forces are required to mix said cells with said gel. In a preferred embodiment this sol-gel is substantially composed of Type I collagen and is available commercially (e.g. VITROGEN produced by Cohesion Corporation of Palo Alto, Calif.). VITROGEN is a purified (i.e. 99.9% pure) pepsin-solubilized bovine dermal collagen dissolved in 0.012N HCl and maintained as a sterile solution.

Another preferred characteristic of this sol-gel is the ability to be cured (or transition) into a solid form. Said solid form being characterized by a substantial inability to be freely poured or mixed. It is not intended that the present invention be limited to any specific mechanism for curing said sol-gel into a solid (e.g. gel) form. In one embodiment, said curing comprises the application of heat. In a preferred embodiment, the sol-gel is cured by the application to a temperature of approximately 37° C. In other embodiments said sol-gel may be cured into a substantially solid form through by exposure to chemicals or ultraviolet radiation.

In another embodiment, the present invention contemplates the use of polypeptide carrier gels.

3. The Integration Layer

The present invention also contemplates a support matrix, seeded with cells, further comprises an integration layer. The integration facilitates the incorporation (in situ) of said support matrix, seeded with cells, into a lesion or defect in the body. In one embodiment, the integration layer is contacted with an organ or tissue in situ. That is to say, the integration layer forms an interface between the (surgically) introduced support matrix seeded with cells and the native in situ tissue or organ of a recipient.

Depending upon the particular type of cells seeded in the support matrix and the tissue into which said cells will be incorporated, the integration layer may provide different functions. In one embodiment the protective layer shields the implanted cell seeded matrix from endocrine or paracrine signals produced by the native tissue of the host. In another embodiment the integration layer may be configured to facilitate the transmission of endocrine or paracrine signals from the native tissue of the host to the implanted cell seeded matrix.

It is not intended that the present invention be limited to any specific mechanism of action for the integration layer. In one embodiment, the integration layer prevents the infiltration of blood vessels and unwanted cells from underlying bone tissue into a chondrocyte seeded matrix implanted into an articulating joint of a host.

In preparing the integration layer of the present invention, a dense collagen barrier can be prepared according to the procedure presented in U.S. Pat. No. 5,206,028, herein incorporated by reference. A porous collagen matrix, having a thickness of about 4 mm to 10 mm, is hydrated using a humidity-controlled chamber (with a relative humidity of 80% at 25° C.) for 60 minutes. The collagen material is compressed between two Teflon sheets to a thickness of less than 0.2 mm. The compressed material is then cross-linked in a solution of 0.5% formaldehyde, 1% sodium bicarbonate at pH 8 for 60 minutes. The cross-linked membrane is then rinsed thoroughly with water, and freeze-dried for about 48 hours. The dense collagen barrier has an inner construction of densely packed fibers that are intertwined into a multilayer structure.

In another embodiment, the integration layer is prepared from collagen-based dispersions or solutions that are air dried into sheet form. Drying is performed at temperatures ranging from approximately 4 to 40° C. for a period of time of about 7 to 48 hours.

In another embodiment, the integration layer is comprised of a co-polymer of polyethylene glycol and collagen that slowly absorbs liquid and slowly biodegrades. The adhesive nature of the co-polymer of polyethylene glycol and collagen may allow the system to be more efficiently placed into, and adhere to, a lesion or defect.

It is not intended that the integration layer recited in the present invention be limited to a co-polymer of polyethylene glycol and collagen. For example, in other embodiments, the integration layer or layers of the system may be comprised of collagen, fibrin, agarose, alginate, chitin, polylactic acid, polyglycolic acid, co-polymers polylactic and polyglycolic, and co-polymers of collagen and fibrin. In addition, the integration layer may further include materials to promote, stimulate, or inhibit growth and development of specific tissues and cells.

Examples of such materials include (but are not limited to): demineralized bone powder, growth and development factors such as bone morphogenic proteins; epidermal growth factors; enzymes that stimulate extra-cellular matrix alteration, such as chondroitinase ABC (U.S. Pat. No. 5,916, 557, herein incorporated by reference); and pro-angiogenic factors such as vascular endothelial cell growth factor (VEGF).

In embodiments of the present invention designed to promote vascularization, the integration layer of the present invention may contain anti-thrombogenic factor such as heparin, or highly negatively charged artificial materials such as styrene-ethylene or butylene-ethylene co-polymers that produce an anti-thrombogenic effect.

In another embodiment of the present invention designed to promote the formation of bone tissue (e.g. wherein osteoblasts are seeded in the support matrix) the integration layer may contain osteogenic factors and/or demineralized bone powder to stimulate the subchondral tissue in situ.

4. The Protective Layer

The present invention also contemplates a support matrix, seeded with cells, further comprising a protective layer. The protective layer encapsulates the outer surface of a cell seeded support matrix. The protective layer insulates a cell-seeded support matrix from the mechanical and physiological trauma that, in some applications, is associated with the implantation of a cell seeded matrix into a host; while simultaneously allowing nutrients to move into said cell seeded matrix. In one embodiment, the protective layer is applied to the cell-seeded matrix before and/or after said matrix is removed from a tissue processor.

In a preferred embodiment, the protective layer comprises a proprietary solution, designated CT3, that is manufactured by Cohesion Technologies of Palto Alto, Calif. that is applied over the surface of a chondrocyte seeded matrix that has been removed after a given culture period in a tissue processor. In one embodiment, a surgeon applies this aerosolized CT3 to subchondral bone in situ. In placing the cellular support layer, a surgeon places the polymer material in the lesion and, without waiting for it to fully polymerize, places the neo-cartilage into position. In this way, the layer facing subchondral bone seals-off the subchondral bone and holds the cellular support layer (e.g. neo-cartilage) in place. The outer protective layer comprising said polymer is then applied in a form that rapidly polymerizes, and is applied in such a manner as to keep it below the articulating surface of the joint to prevent it from being displaced by friction.

In one embodiment, once the system is delivered or implanted into the defect or target lesion, the protective layer shields the new tissue from forces or processes directed towards it from the functional surface, thereby, facilitating the integration of the cellular support with the native tissue surrounding the lesion. For example, when used to protect implanted neo-cartilage, this protective layer can substitute for other types of protective surgical interventions rendering unnecessary the need for the removal of a thin layer of the patient's periosteum from a canalicular bone, and its subsequent securing in place over the system to contain the neo-cartilage.

In a system for producing neo-cartilage, it is further desirable for the protective layer to be positively charged or neutrally charged so as to chemically contain the natural matrix produced by the neo-cartilage as it develops and produces negatively charged components such as chondroitin sulfate and other glycosaminoglycans.

The protective layer of the system may take different forms. Utilization of one form over the other depends on the nature of the lesion and the lesion site to which the neo-tissue is to be delivered, returned, or implanted. In one embodiment the present invention contemplates a lesion or portion of a lesion, in situ, with said protective layer to create a lining and subsequently contacting a support matrix seeded with cells with said lining.

It is not intended that the present invention be limited to a multi-layered system comprising a protective layer made-up of any specific material. For example, in one embodiment, the protective layer comprises an adhesive sealant that is applied by the physician or surgeon after placing the integration layer and cellular support layer into the lesion, and is, therefore, not attached to the system at the time of initial seeding of cells. In order to form an effective seal, it is desirable for the adhesive sealant to be sprayed or applied with an implement such as a large bore syringe such that the adhesive sealant may be easily manipulated by the practitioner prior to the polymerization (or setting) of the co-polymer.

It is further desirable that this material (i.e. sealant) be able to resist 0.01–15.00 MPa of stress. The material used for this application should be a biologically sound polymer that will eventually biodegrade in the body. An example of a material that is preferred is a co-polymer (or construct) of polyethylene glycol and collagen. Indeed, for embodiments of the present invention wherein chondrocytes are seeded into a collagen matrix, collagen-based sealants are preferred. Some of the advantages of using such a co-polymer (or construct) in the protective layer include that said co-polymer is effective, safe, strong and durable, and that it may also be used by the physician as a surgical sealant after the delivery of the multi-layered system or matrix (and the corresponding cells or neo-tissue) into the target lesion.

In another embodiment, the outer/protective layer comprises a protective layer of a sealant (i.e. material) sprayed on the surface of the multi-layered system prior to culturing said system, and is then reinforced with more of the same material once it is placed in the lesion.

In another embodiment, any of the rapid gelling biocompatible polymer compositions described in U.S. patent application Ser. No. 20010055615 (corresponding to Ser. No. 09/293,708) to Wallace (Published Dec. 27, 2001), now U.S. Pat. No. 6,312,725, herein incorporated by reference may be used as the protective layer in the present invention.

In yet another embodiment, the protective layer comprises a rigid, but flexible, material that can be applied by wedging it into a lesion site, effectively sealing-off the lesion and further fulfilling the protective function. Said embodiment may be referred to as a wedging protective layer. Examples of materials suitable for use in this embodiment include, but are not limited to, forms of polylactate or polylactic-polyglycolic acid co-polymer, and a non-woven condensed structure of N-glucosamine of varying degrees of acetylation. The present invention contemplates the use of such materials whether used individually or in combination. Moreover, the present invention contemplates further embodiments in which the adhesive sealant (referred to above) may also be used in conjunction with said wedging protective layer as an extra sealant around the periphery of the inserted system.

III. Tissue Culture Devices and Tissue Processors

1. Standard Incubators

The methods of the present invention employ a variety of tissue culture devices. Standard tissue culture incubators and incubation environments are used to expand (or multiply) cells harvested from tissues or organs. In a preferred embodiment, this expansion of cells is associated with the removal of dead cells and cellular debris (e.g. residual native extracellular matrix). That is to say, standard tissue culture techniques may be used to select out and multiply a desired population(s) of cells. These expanded cells may then be incorporated into the three dimensional cellular support matrices recited in the present invention. In a preferred embodiment, for example, chondrocytes harvested from articular cartilage are expanded in culture. These expanded chondrocytes are then seeded into the cellular support matrix to form a seeded matrix. This seeded matrix may then be placed into a tissue processor.

2. Tissue Processors

A tissue processor has the capacity to regulate/modify tissue culture conditions including the application of constant or cyclic hydrostatic pressure, the recirculation of media, and the regulation of oxygen concentration. In a preferred embodiment said tissue processor is the Tissue Engineering Support System (TESS) described in published U.S. patent application Ser. No. 20010021529 (corresponding to U.S. patent application Ser. No. 09/796,422) assigned to Takagi Industrial Co. Ltd and, herein, incorporated by reference.

The TESS processor provides an apparatus for cultivating cells or tissue comprising: a culture unit having a culture chamber containing cells or tissue and culture medium; a pressure application means for applying pressure to the cells or tissue in the culture chamber; and a culture medium supply means for the continuous or intermittent delivery supply of culture medium to the culture unit. (See FIG. 1 and corresponding text of U.S. patent application Ser. No. 09/796,422). The TESS processor may also comprise a control means (e.g. pressure relief valve) for controlling the pressure application means or culture medium supply means. Generally, the pressure applied to the cells or tissue is set depending on the type of cells or tissue to be grown. The TESS processor further comprise a means capable of absorbing gases such as nitrogen, carbon dioxide, and oxygen. Also, the TESS processor further comprises a hermetically sealed space including a heating means and a humidifying means.

3. Applications of Tissue Processors

Certain cells are extremely difficult to grow in three-dimensional (3-D) culture such that they may form a neo-tissue (e.g. neo-cartilage). The TESS processor not only facilitates the growth and culture of these difficult to grow cells but it allows a mixed culture of cells to be grown together. These mixed populations of cells may be cultured in the TESS under conditions such that they self-organize into a tissue construct that approaches the histological organization of an in situ organ. While it is not intended that the present invention be limited by any specific tissue culture mechanism or protocol, the TESS perfuses medium under pressure, thereby, facilitating the delivery of oxygen and nutrients to the interior of cell seeded 3-D matrices.

Neo-tissues could be composed of healthy human or cancerous cells. Cancerous cells could be used as a model system for screening anticancer and allow investigator to develop, in vitro, the optimum drug regimen in advance of clinical trials For example, a 3-D neotissue comprised of epithelium-derived secretory cells and mesoderm-derived stromal cells could approximate the morphology of in situ prostate tissue. Such a "prostate like" neo-tissue could allow an investigator to screen, as a prostate tumor repression drug, the many analogues of vitamin D.

Furthermore, these 3-D cultures could be comprised of a cancerous cells (from a metastasized tumor in one organ) and "normal" cells that are the target for the metastasizes of said cancerous cells, thereby, facilitating the study metastatic interactions. Such systems would be especially important in cases where cancer mortality results not from a primary cancer of epithelial secretory cells (e.g. in prostate or breast cancer), but from the transformation of bone by interaction with migrating cells from the primary cancer site. Such a 3-D culture would be valuable in evaluating the combinatory drugs regimens indicated for prostate metastasis (e.g. androgen repressors/chemotherapeutic agents such as carboplatin).

IV. Overview of the Formation of Neo-Tissues

The present invention provides methods for the formation of neo-tissue using the components of the multi-layered system described above. More specifically these components are combined and reacted under conditions such that a viable three dimensional neo-tissue is produced. The combination and reaction conditions for these components may be varied according type of neo-tissue produced and the intended application for this same neo tissue. In a preferred embodiment, however, neo-cartilage is produced according to the following scheme.

1. Isolation of Chondrocytes From Source Tissue

Chondrocytes were enzymatically isolated from cartilage harvested under sterile conditions from the hind limbs of 6-month old swine. The femur was detached from the tibia and the trochlea head exposed. Strips of cartilage were removed from the trochlea using a surgical blade. The cartilage was minced, digested in a 0.15% collagenase type I solution in DMEM: Nutrient Mixture F-12 (DMEM/F-12) 1:1 mixture with 1% penicillin-streptomycin (P/S) and gently rotated for 18 hours at 37° C. Chondrocytes were collected and rinsed twice with PBS by centrifugation at 3000 rpm for 5 min. Chondrocytes were re-suspended in DMEM/F-12 supplemented with 10% heat-inactivated fetal bovine serum (FBS) and 1% P/S.

2. Seeding Cells in the TESS Matrix

Isolated chondrocytes were incubated for a period of five days at 37° C. in a standard incubator. Cells were then collected by trypsinization. A cell suspension of 150,000 cells in 18 ul of VITROGEN solution was seeded per matrix (said matrix having an approximate volume of 19 ul) with nine matrices per group. It is not intended that the present invention be limited to specific cellular support matrix size or shape or number of cells. Indeed, in one embodiment of the present invention, the seeded matrix may be scaled-up to an increased volume (wherein approximately 1 ul of the above described cell suspension is seeded in 1 ul of matrix). The control group matrices were incubated in a 37° C. incubator and the test group was incubated in the TESS. (See, Example 1 and Table 1).

In another experimental example, isolated chondrocytes were incubated for a period of five days at 37° C. in a standard incubator. Cells were then collected by trypsinization. A cell suspension of 300,000 cells in 18 ul of VITROGEN solution was seeded per matrix (said matrix having an approximate volume of 19 ul) with eight matrices per group. It is not intended that the present invention be limited to specific cell numbers or cellular support matrix size or shape. Indeed, in one embodiment of the present invention, the seeded matrix may be scaled-up to an increased volume (wherein approximately 1 ul of the above described cell suspension is seeded in 1 ul of matrix). The control group matrices were incubated in a 37° C. incubator and the test group was incubated in the TESS. (See, Example 2 and Table 2).

3. Biochemistry (DMB Assay)

At the end of the culture six matrices from each group were used in the biochemistry assay. Briefly, the matrices were transferred to microcentrifuge tubes and digested in 300 μl of papain (125 μg/ml in 0.1 M sodium phosphate, 5 mM Disodium EDTA, and 5 mM L-cysteine-HCL) for 18 hours at 60° C. GAG production in the matrices was measured using a modified dimethylene blue (DMB) miocroassay with shark chondroitin sulfate as a control (Reference: Connective Tissue Research, 1982, vol. 9, pp 247–248)

4. Histology

The remaining matrices from each group were fixed in 4% paraformaldehyde. The matrices were processed and embedded in paraffin. 10 μm sections were cut on a microtome and stained with Safranin-O (Saf O).

V. Preferred Protocols for Neo-Tissue Growth

The present invention contemplates protocols for the growth (i.e. in vivo, ex vivo, and in vitro) of neo-tissues, using the component of the multi-layered system described in the instant application. In preferred embodiments, the TESS processor is used to deliver constant or cyclic hydrostatic pressure to the cell-seeded matrix. In this preferred embodiment, these cell-seeded matricies are maintained in resting phase (in one example in a standard incubator or TESS processor maintained at 37° C. at atmospheric pressure) subsequent to constant or cyclic hydrostatic pressure exposure.

1. Production of Neo-cartilage

In a preferred embodiment, autologous pig chondrocytes are seeded into the cellular support matrix and incubated under cyclic hydrostatic pressure at 37° C. and 5% $CO_2$. In this preferred embodiment, said cyclic hydrostatic pressure is approximately 3.0 MPa of pressure at 0.5 Hz. In this preferred embodiment the duration of said cyclic pressure is approximately 6 days followed by a resting phase of 12 days in an incubator maintained at 37° C. at atmospheric pressure. At the end of this resting phase, the matrices were harvested for biochemical and histological analysis as described in Example 1 and Example 2.

2. Alternative Protocol

In another embodiment, the present invention contemplates an algorithm for the growth (i.e. in vivo, ex vivo, and in vitro) of cells, using the components of the present invention, involving the application of hydrostatic pressure to isolated in situ cartilage (or chondrocytes adhered to a matrix) and subjected to the regimen comprising the cyclic application of hydrostatic pressure for about 1–8 hours followed by about 16–23 hours of recovery period.

3. Reduced Oxygen Concentration

In an alternative embodiment the chondrocytes-seeded cellular support matrix described above may be cultured under reduced $O_2$ concentration (i.e. less than 20% saturation) during formation of neo-cartilage in the TESS processor. While it is not intended that the present invention be limited to any specific mechanism, the reduced oxygen concentration of cartilage, observed in vivo, may be due to its (normal) lack of vascularization which produces a lower (as compared to the adjacent tissues) oxygen partial pressure. In one embodiment, neo-tissues are cultured under oxygen concentration between approximately 0% and approximately 19% saturation. In another embodiment, said oxygen concentration is approximately 2% saturation.

VI. Medical Applications

The compositions and methods of the present invention are suitable for use in a variety of medical applications. In one embodiment, the heat-cured, cell-seeded matrix described in the present invention may be implanted in vivo to repair damaged cells or tissue. In another example, the heat cured cell seeded matrix of the present invention may replace or augment existing tissue or to join together biological tissues or structures as described below.

1. Tissue Repair Applications

It is not intended that the use of the compositions and methods of the present invention be limited to the repair, replacement, reconstructed or augmentation of any specific tissue (or cell) type. For example, in one embodiment, damaged cartilaginous tissue is repaired, replaced, reconstructed or augmented. In another embodiment, tissue defects left by tumor, trauma, infection, or congenital malformation (involving various tissue or cell types) are repaired, replaced, reconstructed or augmented.

A. Cartilage Repair

While the present invention provides composition and methods for the repair of full thickness cartilaginous defects, they may also be directed to the repair of partial thickness defects. Further, the systems and methods of the present invention may be combined with techniques for forming templates of defect areas so that customized formed neo-tissues may be produced that are dimensionally adapted and tailored for a particular patient's defect. In addition, the systems and methods of the present invention may be used to create entire cartilaginous structures such as menisci, or may be used to create materials for partial or total replacement of an articular surface. In other embodiments, cartilaginous neo-tissues (i.e. neo-cartilage) according to the present invention may be available for combining with alloplastic materials to form artificial joints. In one embodiment, the cartilaginous neo-tissues (i.e. neo-cartilage) described in the present invention will repair and/or replace tendons and ligaments. In a specific embodiment said ligament is the anterior cruciate ligament (ACL). In another embodiment, the cartilaginous neo-tissues (i.e. neo-cartilage) described in the present invention will repair and/or replace vertebral disks.

The compositions and methods of the present invention may be adaptable to formation of neo-tissue constructs combining, for example, formed cartilage and formed bone to be used for replacement of an entire articular surface including sub-chondral bone, or will be used for replacement of a cartilage covered small bone such as may be found in the wrist. Whether used for forming cartilaginous neo-tissue, or for forming neo-tissue constructs, these compositions may be fashioned into implantable structures for total joint replacement, and for hemi-joint replacement in small joints such as those in the hand or the temporomandibular joint.

In another embodiment, these systems and methods may be used for creating an implantable, full-thickness, cartilaginous neo-tissue to be placed in a large weight bearing joint such as the knee. Arthroscopic procedures may be advantageously utilized in harvesting native chondrocytes to be incorporated in a neo-tissue formed by these compositions and methods.

In one embodiment of the present invention, a first arthroscopic procedure will be employed to evaluate the extent of the potential cartilaginous defect and to harvest native chondrocytes for subsequent culturing and delivery into the cellular support matrix described in the present invention. Based on a template formed at the time of this first arthroscopic procedure, or based on measurements made during the procedure, a dimensional model will be formed of the anticipated defect and the neo-tissue will be formed to conform in size and shape to this model A second arthroscopic procedure will be carried out to debride a damaged area of the in situ native cartilage and to replace the damaged area with the neo-cartilage prepared according to the present invention.

Other adaptations of conventional surgical techniques will be employed at other anatomic sites for harvesting native cartilage cells, for debriding damaged cartilage tissue, for creating a defect within the host articular surface (e.g. including a complete excision of a joint surface or a partial excision of a joint surface), for implanting neo-tissue into the host defect and for retaining the neo-tissue in that site.

B. Tissue Defect Repair

Defects left by tumor, trauma, infection, or congenital malformation, are well-known in the medical and surgical arts. Reconstruction of such defects may require full-thickness tissue replacement, or may require replacement of tissue constructs. For example, in one embodiment, an excision taken from the lower eyelid (e.g. in the case of a basal cell carcinoma) may need to be reconstructed by an extensive flap procedure that "employs" adjacent tissues or tissues from the upper lid. Alternatively, grafting procedures using the other lids or nasal septum as donor sites may be employed (despite the fact that there may be donor site problems, and that some local tissue rearrangement will be required at the reconstructed area).

The present invention may be adapted to repair these defects. For example, a neo-tissue construct providing both neo-cartilage and a covering layer (conjunctival or epidermal) will be positioned in such a defect to simplify the reconstructed task. Alternatively, a neo-tissue comprising all three layers of eyelid tissue could omit the need for any substantial local tissue rearrangement. A neo-tissue comprising neo-cartilage would obviate the need for harvesting a cartilage graft from elsewhere with the consequent donor site risks.

In another embodiment, a nasal-septal deformation defect will be repaired using neo-cartilage. Repair of persistent fistulas after cleft palate procedures may also be amenable to treatment with the neo-cartilage described in the present invention. These fistulas left from cleft palate repairs may require reconstruction using a tissue construct with two outer mucosal layers covering an inner bony layer.

In another embodiment, the neo-tissues described in the present invention will also be adapted to difficult reconstructive problems. Using the compositions and methods of the present invention oral mucosa could be produced in significant quantities to fill or surface intraoral defects with a specialized tissue having functional characteristics appropriate for the intraoral location. Reconstruction of other specialized areas such as nail beds and articular cartilage for large and small joints may also be undertaken using the compositions and methods of the present invention. The present invention may also provide reconstructive solutions to damaged temporomandibular joint or may be applied to repairing degenerative diseases such as rheumatoid arthritis.

C. Ligament and Tendon

The compositions and methods of the present invention will be adapted to the production of tendon and ligaments in vitro. In one embodiment, this will be promoted by the stretching of ligament and tendon progenitor cells, over a scaffold, ex vivo during the exogenous development of ligament or tendon. The ligaments contemplated by the present invention will be derived from ligament progenitor cells, mesenchymal stem cells, or fibroblasts, especially fibroblasts derived from the sheath cells surrounding ligament and tendon, or fibroblast or tenocytes derived from the ligament or tendon themselves. Autologous ligaments and tendons may be used to replace damaged ligaments and tendons in a patient's own body without fear of immune response or other adverse response.

The stretching scaffold, referenced above, may be considered another layer in the multiplayer composition described in the present invention. This scaffold will allow the progenitor cells to be stretched ex vivo (for example in a modified TESS processor) so as to apply a physical stimulus which causes them to produce proteins and matrix components which are consistent with true neo-ligaments or neo-tendons.

In one embodiment, the stretching scaffolding will consist of a fibrous material that can resist tensile stresses that fall within the range of tensile stresses to which cartilage and ligament are normally subjected in the course of lifetime. More specifically, the fibrous material may resist a range of tensile stresses which are necessary to induce said cells to begin producing the normal gene products in the correct ratio that differentiate ligament and tendon from other tissues or organs, and that allow these gene products to take on the orientation and physical condition, such that a healthy and morphologically sound ligament or tendon may develop on such scaffolding. Also, the fibrous material should have a degree of elasticity which can accommodate the amount of progenitor cell stretching required to induce said cells to form neo-ligament or neo-tendon.

The ligament and tendon developed upon such scaffolding will acquire a tensile strength, an elasticity and a structure to support bone and muscle in vivo, which is equivalent to the tensile strength and structure of ligament and tendon developed within the body during the normal course of growth and differentiation. The scaffold is also designed so that once the neo-ligament or neo-tendon is sufficiently functional, the scaffolding will reintroduce the ligament or tendon into the lesion and support until it integrates in the body. In one embodiment the scaffolding will degrade after implantation.

In one embodiment, the cells placed on the scaffolding will be chosen from cells at a stage in their developmental life such that (when on placed on the scaffolding and subjected to the physical and chemical conditions of a 3-D tissue culture apparatus designed to induce differentiation of cartilage and ligament) these cells will produce substantially all of the gene products elaborated by morphologically-sound ligaments or tendons.

In one embodiment, the scaffolding is selected from variety of materials, including but not limited to, polyesters (including polyalkynoates), polyglycolates, polylactates, biodegradable suture materials. Other materials may also be suitable so long as these materials can safely degrade within the body, and so long as the products of the degradation do not interfere with the normal metabolic function of the cartilage and ligament or the surrounding tissue.

The physical structure of the scaffold need be consistent with its intended function (e.g. the uniform application of tensile stress at the cellular (micrometer) level). These stresses are very mild compared with the stresses place upon the mature cartilage or ligament. It is also important that the fibrous structure resists rupturing at the required tensile strengths. In one embodiment, fibers of 1–10 micrometer diameter will be woven into a variety of weave patterns including, but not limited to a solid weave, a hollow centered weave (such as the Chinese puzzle weave) such that the application of tensile stress to the ends of the scaffold will produce a uniform stretching of the surface of the scaffold. To produce a ligament with its own bone anchoring points it would be possible to incorporate at the polar ends of the scaffold such substances as demineralized bone powder, which under the correct physical stimulus would be induced to form bone to be incorporated into existing bone when placed in situ in the body.

D. Other Applications

The compositions and methods of the present invention may also be used as a model for elucidating the mechanism of certain diseases. For example, in one embodiment, the multi-layered systems of the present invention may also be used as models for the study of physiologic or pathologic conditions in vitro. For example, in one embodiment of the invention, the system may be used as a model for the blood-brain barrier. In another embodiment, a three-dimensional culture of mucosal epithelium (produced by using the compositions and methods of the present invention) may be used as a model system to study herpes virus or papilloma virus infection. Such a model system could be used to test the efficacy of anti-viral medications.

Alternatively, the compositions and methods of the present invention may be used for studying the pharmacokinetics of various drugs and growth factors. For example, the neo-tissues described in the present invention may also be used for the in vitro screening of cytotoxic compounds, allergens, growth and regulatory factors, pharmaceutical compounds. To this end, the neo-tissue may be maintained in vitro and exposed to the compound to be tested. For example, the activity of a cytotoxic compound can be measured by its ability to damage or kill cells in culture. This may be readily assessed by known vital staining techniques.

The effect of growth or regulatory factors may be assessed by analyzing the cellular content of a neo-tissue, for example, by total cell counts and/or differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed. For example, drugs that increase red blood cell formation can be tested on three-dimensional bone marrow cultures. Drugs that affect cholesterol metabolism, by lowering cholesterol production for example, could be tested on the three-dimensional liver system. Three-dimensional cultures of tumor cells may be used as model systems to test, for example, the efficacy of anti-tumor agents.

The compositions and methods of the present invention may also be used to aid in the diagnosis and treatment of malignancies and diseases. For example, a biopsy of any tissue (e.g. bone marrow, skin, liver, etc.) can be taken from a patient suspected of having a malignancy. If the biopsy cells are cultured in system of the invention, malignant cells may be clonally expanded during proliferation of said culture, thereby increasing the chances of detecting a malignancy and, therefore, increasing the accuracy of the diagnosis and timeliness of treatment. Such an application of the present invention may be especially useful in diseases such as AIDS where the infected population of cells is depleted in vivo. Moreover, in such a case, the patients culture could be used in vitro to screen compounds (e.g. cytotoxic compounds or pharmaceuticals) in order to identify those that are most efficacious (i.e. those that kill the malignant or diseased cells, yet spare the normal cells). These agents could then be used to therapeutically treat the patient.

VII. Alternative Embodiments

While certain embodiments of the multi-layered system for producing neo-tissues or neo-tissue constructs comprise a three-layer construction, the present invention also contemplates multi-layered systems comprising more than three layers.

For example, in producing a neo-tissue or neo-tissue construct, the layers of the multi-layered system may be arranged to include: a bottom, tissue attachment layer; a second layer supporting a biologic matrix, wherein resides a first type of tissue cell; a third, integrating layer deployed atop the second layer to integrate the second layer with an additional layer of biologic matrix, wherein resides a second type of tissue cell; and a top, protective layer arranged on top of the additional layer of biologic matrix. Such an arrangement could provide for a tissue construct including a layer of cartilage protected by a layer of mucosa. Preferably, the integrating layer would be formed of a material that would enhance the normal attachment of the cartilage layer and the mucosal layer so that their unitary behavior under physiologic conditions would replicate the behavior of the native tissue.

More complex structures with multiple cellular support matrices seeded with cells from at least two tissue types are also contemplated, with integrating layers positioned between each matrix. For example, a tissue construct of the nasal septum could be fabricated (according to these principles) with an outer mucosal layer, an inner cartilaginous layer, and a second outer mucosal layer.

In another embodiment, a neo-tissue construct according to the present invention may be produced that includes the three layers of the nasal septum.

In other embodiments, the neo-tissues described by the present invention may be fashioned into a variety of shapes. For example, tubular structures such as blood vessels, ducts or other specialized conduits (e.g. ureter, ureter, esophagus, etc.) may be formed by sculpting a neo-tissue around a mandrel or other tube forming shape.

In other embodiments the compositions and methods of the present invention could be used to create luminal, tubular or cylindrical structures such as, for example, a multi-layered blood vessel.

In another embodiment, the compositions and methods of the present invention may be used to produce a replica of a tendon or a ligament (i.e. neo-tendon or neo-ligament). The multi-layered system of the present invention may be formed within an external guiding tube to produce a structure that functionally replicates a tendon. To fashion a neo-ligament a seeded cellular support matrix may be inserted into an external guiding tube that would act as a shaping template for the neo-ligament. In another embodiment, a slowly degrading mandrel may be employed using a material like polyglycolic lactic acid (PGLA).

In yet another embodiment, the compositions and methods of the present invention may be used to form a tissue replica of oral mucosa (i.e. neo-mucosa). The system for forming oral mucosa may include a matrix for supporting the growth and differentiation of keratinocytes, and may also include a protective layer directed towards the functional surface of the oral mucosa (i.e., towards the oral cavity). Said protective layer would be constructed to shield the underlying cellular support layer from the chemical and enzymatic impact of contact with a saliva, as well as, from physical forces inherent in the intraoral anatomic location.

The system for forming oral mucosa may further include an integration layer adapted for facilitating the attachment of the cells formed in the cellular support layer to the underlying bone. The integration layer may, for example, include osteogenic factors or demineralized bone powder for stimulating and inducing bone and periosteal ligament development. As another example, this layer may comprise cadaveric dermis embedded in (or layered with) osteogenic factors or demineralized bone powder.

In another embodiment, the compositions and methods of the present invention may be used to form a tissue replica of the skin (e.g. neo-epidermis or neo-dermis). For example, a cellular support layer may be provided that allows the growth and differentiation of keratinocytes into stratified, keratinized epithelium. Affixed to said cellular support layer, may be an integration layer that further contains fibroblasts, growth factors and appropriate nutrient materials capable of producing a tissue replica of the dermis (i.e. neo-dermis). The integration layer may be further adapted to attaching the skin tissue replica to its underlying tissue bed.

A neo-tissue of skin may has numerous medical uses. For example, such a neo-tissue may be used in acute or reconstructive burn surgery, in the reconstruction of excisions, or in the treatment of chronic wounds or pressure sores.

In a further embodiment, the multi-layered system of the present invention is fashioned into an in vitro tissue construct to screen cytotoxic and pharmaceutical compounds, and to assess biological responses to cytokines and growth/regulatory factors. For example, a tissue construct which approximates the form and function of a human or non-human animal prostate gland (i.e. a neo-prostate or neo-gland as characterized by a composite of stromal and glandular cells) may comprise a system, which includes a protective layer and multiple cellular support layers. In such an embodiment, the protective layer may function to contain the neo-organ within a desired volume and help it retain its shape and integrity. Such a system may optionally have an integration layer. The integration layer may anchor the system, for example, to the in vitro culture substrate employed (e.g., a culture dish, flask, slide, etc.). Each cellular support layer may provide a principal cell type present in (and harvested from) the native prostate gland. Examples of such cell types include, but are not limited to, prostate gland secretory epithelium, stromal smooth muscle, and fibrous connective tissue. In order to form a neo-organ with dimensions approximating that of the native prostate gland, a multi-layered system may be fashioned to include a protective layer, an optional integration layer, and a plurality of cellular support layers. Such a plurality of cellular support layers may comprise, for example, several sets of three cellular support layers stacked upon one another and deployed within a single system. The combination of cell types may approximate the structure and function of the prostate gland in situ.

Experimental

The following examples serve to illustrate preferred embodiments and aspects of the present invention and are not to be construed as limiting the scope thereof.

Example 1

This example provides one instance in which tissues were formed in vitro in one embodiment of the present invention. Briefly, swine articular chondrocytes (sACs) were enzymatically isolated from cartilage with type I collagenase. The cells were suspended in collagen (VITROGEN) as described above and wicked into the honeycombed sponge element of the cellular support matrix (e.g. the TESS matrix). The cells in their 3-D support (i.e. the TESS matrix) were incubated at 37° C., 5% $CO_2$ and 20% $O_2$. After 24 hours, some of these cell matrices (i.e. cellular support layers comprising the test group) were transferred to the TESS™ processor and incubated at 3.0 MPa cyclic hydrostatic pressure as described above for 6 days followed by a 12 day resting phase.

The control group comprised of chondrocyte-seeded TESS matrices incubated for 18 days, at 37° C., 5% $CO_2$ and 20% $O_2$ and at atmospheric pressure.

Figure 1:
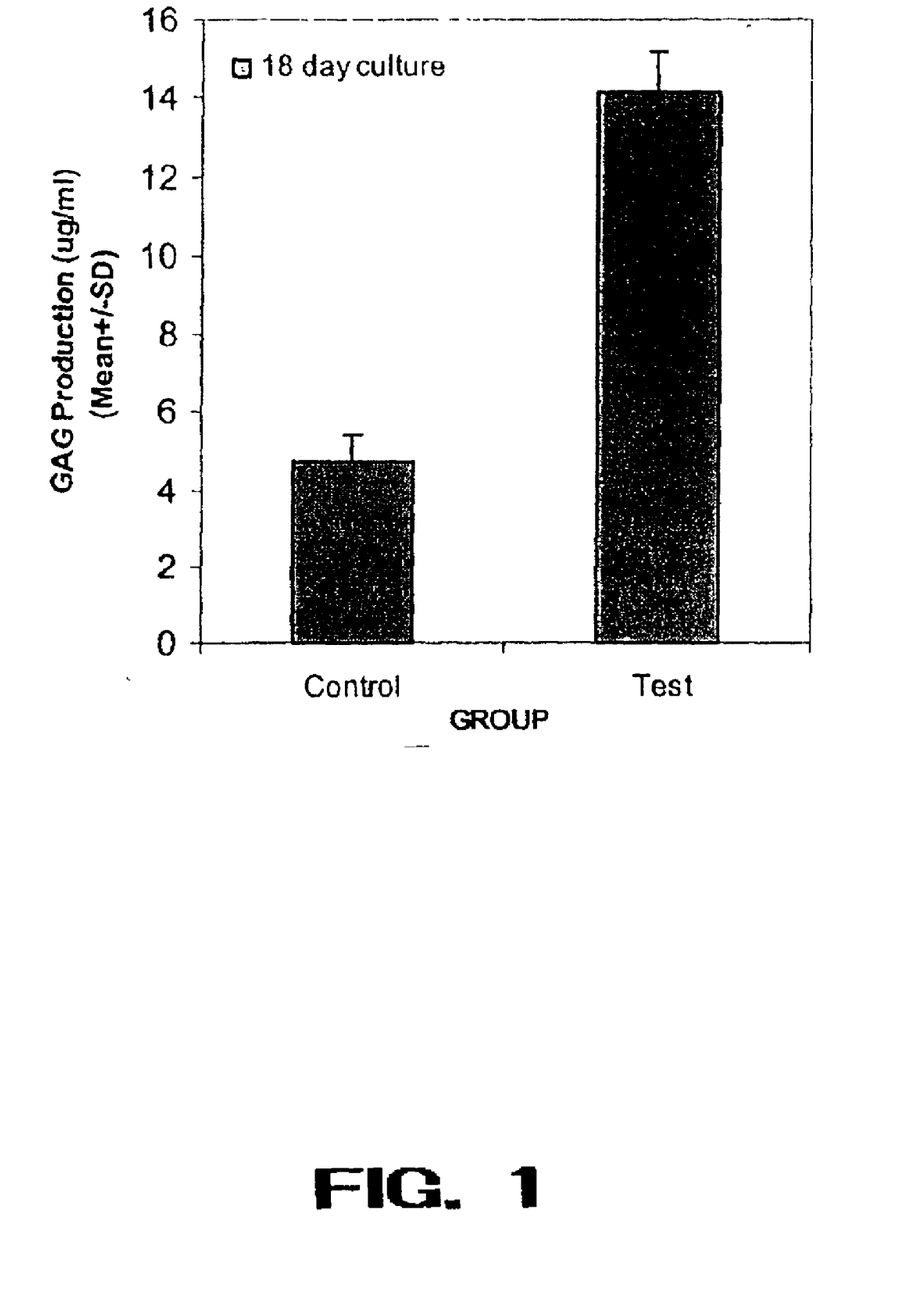
FIG. 1 projects data on the effect of cyclic hydrostatic pressure, as compared to static atmospheric pressure, on glycosaminoglycan (GAG) production by chondrocytes cultured within the TESS matrix. Specifically, this figure shows that there is a 300% increase (p<0.001) in GAG production in TESS matricies in the test group (3.0 MPa CHP at 0.5 Hz) than in the TESS matricies in the control group (atmospheric pressure only).
Figure 2A:
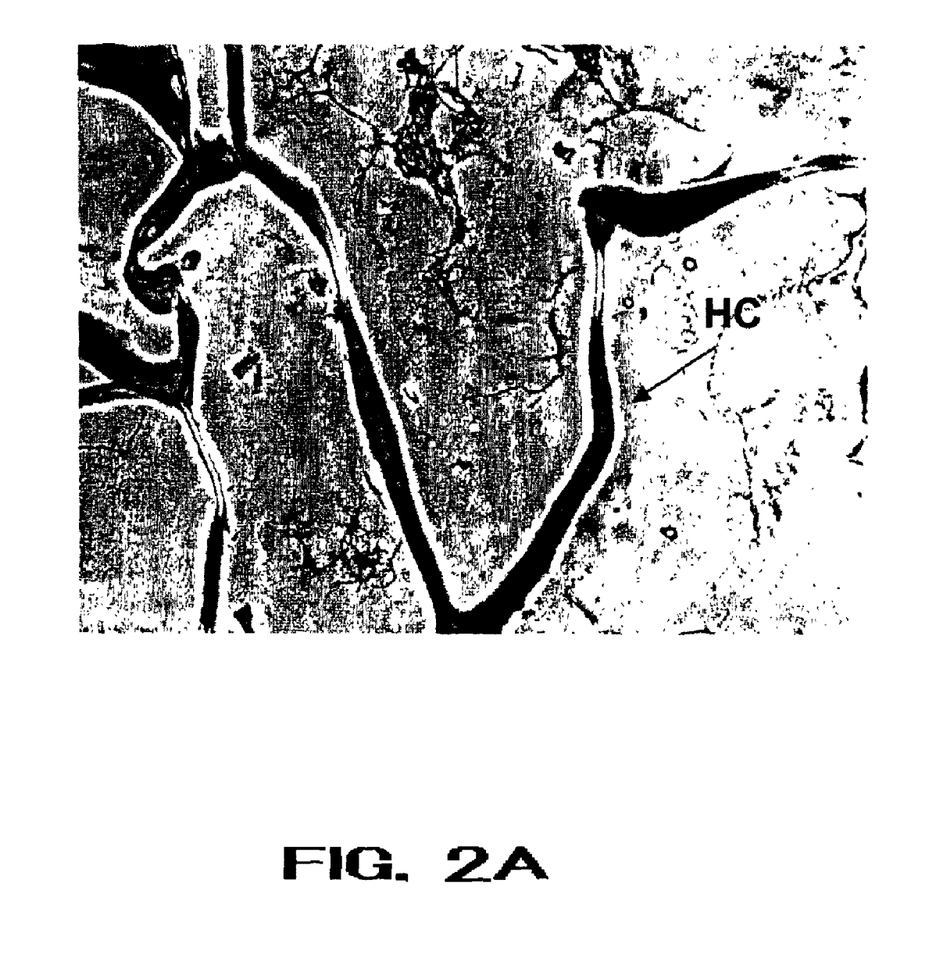
FIG. 2A is a photomicrograph presenting the elaboration of Safranin-O staining of extracellular matrix by chondrocytes, cultured under static atmospheric pressure (control group), within the TESS matrix. In this figure the honeycomb sponge element of the cellular support matrix (e.g. the TESS matrix) is labeled "HC" and an area of extracellular matrix (elaborated by the cultured chondrocytes) is labeled with an "*".
Figure 2B:
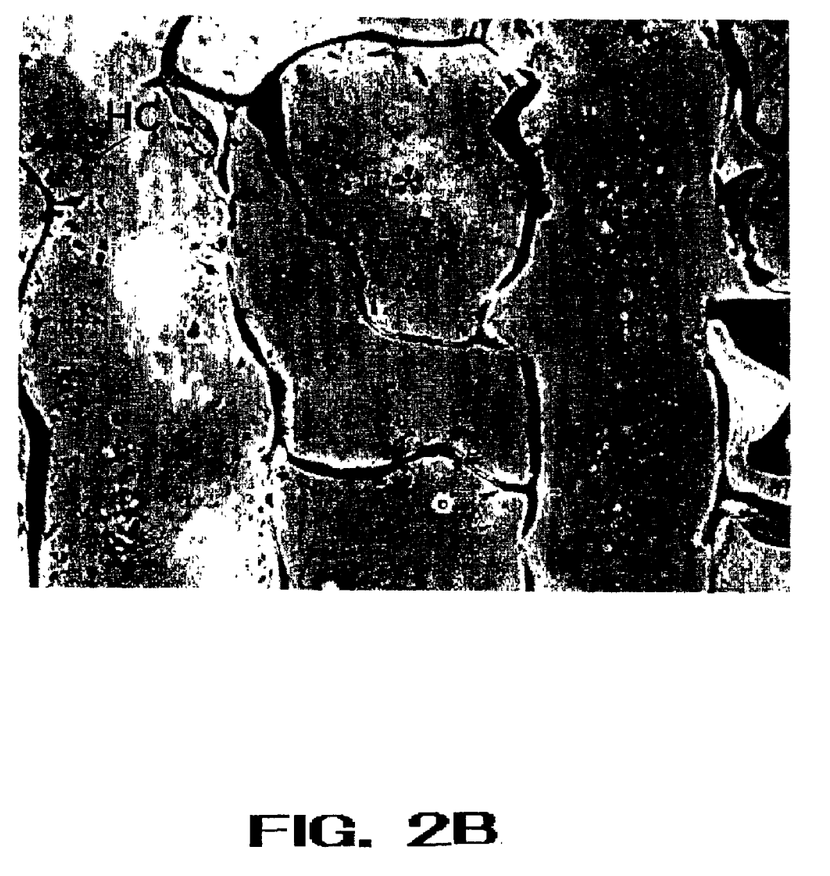
FIG. 2B is a photomicrograph presenting the elaboration of Safranin-O staining of extracellular matrix by chondrocytes, cultured under cyclic hydrostatic pressure (test group), within the TESS matrix. In this figure the honeycomb sponge element of the cellular support matrix (e.g. the TESS matrix) is labeled "HC" and an area of extracellular matrix (elaborated by the cultured chondrocytes) is labeled with an "*".

At the end of the culture period, the matrices were harvested for biochemical and histological analysis as noted in Table 1. For biochemical analysis, glycosaminoglycan (GAG) production was measured using a modified dimethymethylene blue (DMB) microassay. FIG. 1, described in the "Description Of The Drawings" of the instant specification, represents, in graph form, the data set out in Table 1. For histological analysis, formation of neo-tissue was measured by Safranin-O staining. The histology of the control group is illustrated in FIG. 2A. The histology of the test group is projected in FIG. 2B.

TABLE 1

| Group (n = 8 matricies per group) | Pressure Conditions | | | GAG Production ($\mu$g/ml) (mean +/− SD) (n = 6 matricies) |
|---|---|---|---|---|
| | In TESS processor (3 MPa Cyclic Pressure, @ 0.5 Hz) | In Incubator (Atmospheric Pressure) | Total days In culture | |
| Control | — | 18 days | 18 | 4.71 ± 0.71 |
| Test | 6 days | 12 days | 18 | 14.11 ± 1.10 |

NOTE:
1) All cultures were incubated at 37° C., 5% $CO_2$ and 20% $O_2$.
2) In TESS culture, media flow rate was 0.05 ml/min.
3) Two matricies from each group were harvested for histological analysis.

Example 2

This example provides another instance in which tissues were formed in vitro in another embodiment of the present invention. Swine articular chondrocytes (sACs) were enzymatically isolated from cartilage with type I collagenase. The cells were suspended in collagen (VITROGEN) as described above (e.g. 300,000 cells in 18 ul of VITROGEN) and were wicked into the honeycomb sponge element of the cellular support matrix (i.e. the TESS matrix), wherein each matrix had a volume of approximately 19 ul.

The cells in their cellular support matrix were incubated at 37° C., 5% $CO_2$ and 20% $O_2$. After 24 hours, some of these cell matrices (the test group) were transferred to the TESS™ processor and incubated at 3.0 MPa cyclic hydrostatic pressure as described above for 6 days followed by incubation for 12 days at atmospheric pressure at 37° C., 5% $CO_2$ and 20% $O_2$.

The remaining cell matrices comprising the control group were incubated at atmospheric pressure for 18 days at 37° C., 5% $CO_2$ and 20% $O_2$.

Figure 3A:
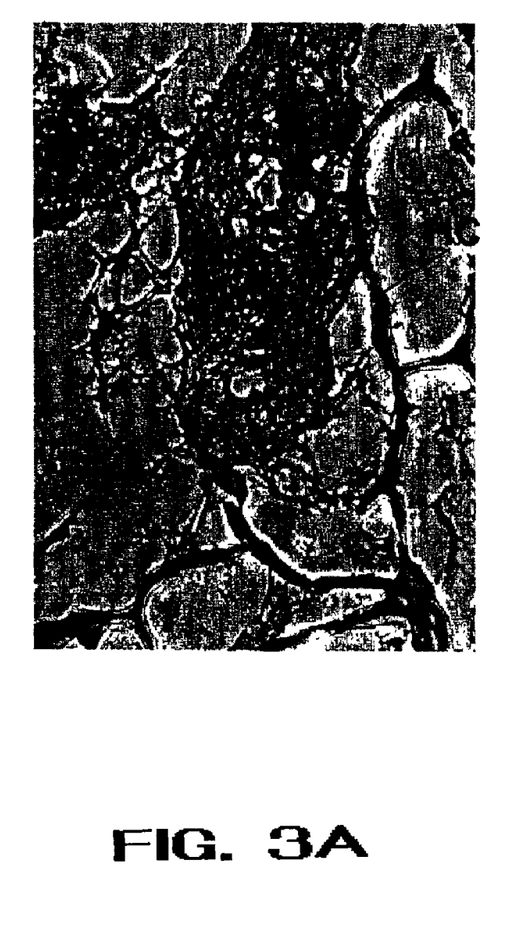
FIG. 3A is another photomicrograph presenting the elaboration of Safranin-O staining extra cellular matrix by chondrocytes, cultured under static atmospheric pressure (control group), within the TESS matrix. In this figure the honeycomb sponge element of the cellular support matrix (e.g. the TESS matrix) is labeled "HC" and an area of extracellular matrix (elaborated by the cultured chondrocytes) is labeled with an "*".
Figure 3B:
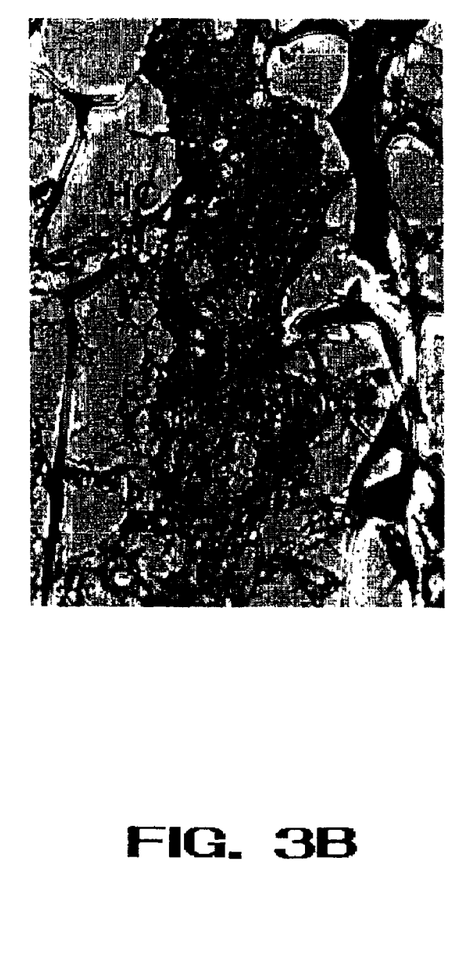
FIG. 3B is a another photomicrograph presenting the elaboration of Safranin-O staining of extracellular matrix by chondrocytes, cultured under cyclic hydrostatic pressure (test group), within the TESS matrix. In this figure the honeycomb sponge element of the cellular support matrix (e.g. the TESS matrix) is labeled "HC" and an area of extracellular matrix (elaborated by the cultured chondrocytes) is labeled with an "*".
Figure 4:
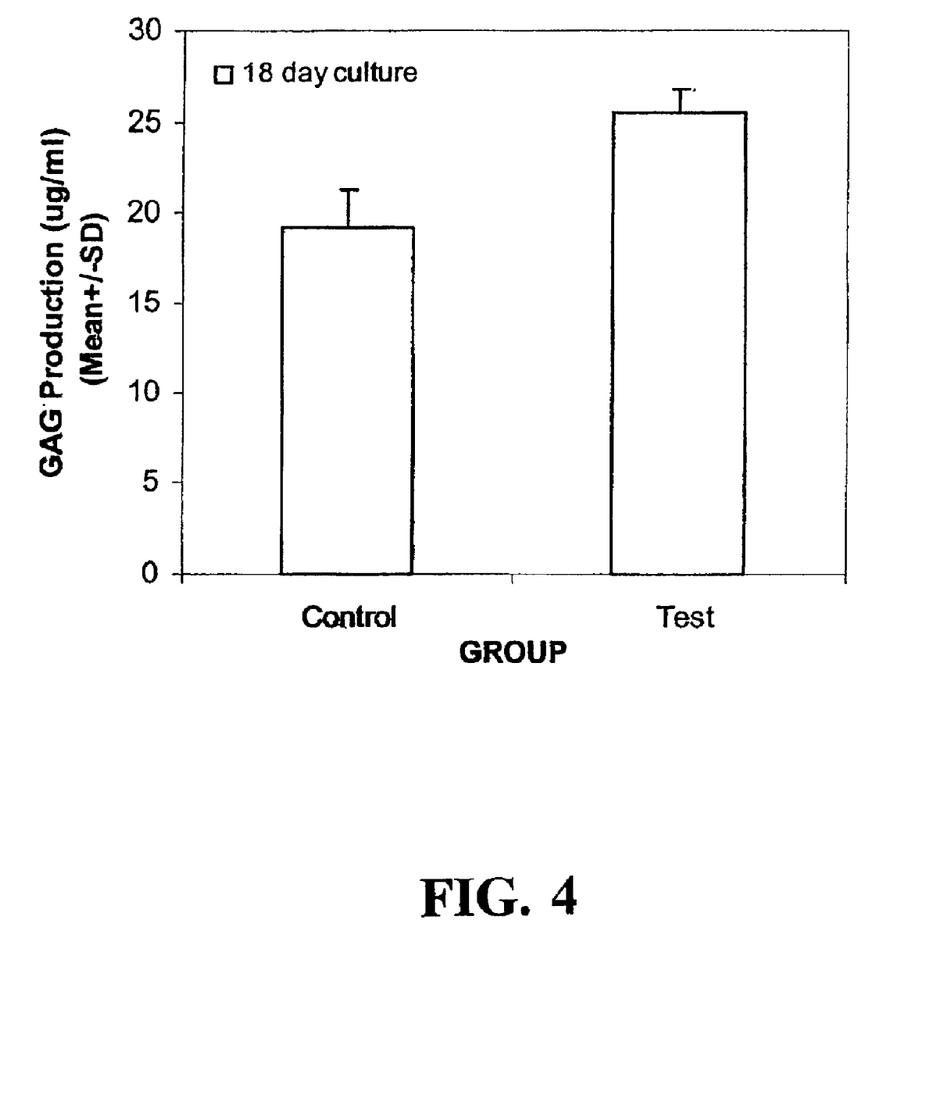
FIG. 4 illustrates data on the effect of cyclic hydrostatic pressure, as compared to static atmospheric pressure, on glycosaminoglycan (GAG) production by chondrocytes cultured with the TESS matrix. Specifically, this figure shows that there is a 132% increase (p<0.006) in GAG production in TESS matricies in the test group (3.0 Mpa CHP at 0.5 Hz) compared to TESS matricies in the control group (atmospheric pressure only).

At the end of the culture period, the matrices were harvested for biochemical and histological analysis as noted in Table 2. For biochemical analysis, glycosaminoglycan (GAG) production was measured using a modified dimethymethylene blue (DMB) microassay. FIG. 4, described in the "Description Of The Drawings" of the instant specification, represents, in graph form, the data set out in Table 2. For histological analysis, formation of neo-tissue was measured by Safranin-O staining. The histology of the control group is illustrated in FIG. 3A. The histology of the test group is projected in FIG. 3B.

TABLE 2

| Group (n = 8 matricies per group) | Pressure Conditions | | Total days In culture | GAG Production (μg/ml) (mean +/− SD) (n = 6 matricies) |
|---|---|---|---|---|
| | In TESS (3 MPa Cyclic Pressure, @ 0.5 Hz) | In Incubator (Atmospheric Pressure) | | |
| Control | — | 18 days | 18 | 19.24 ± 2.14 |
| Test | 6 days | 12 days | 18 | 25.44 ± 1.37 |

NOTE:
1) All cultures were incubated at 37° C., 5% $CO_2$ and 20% $O_2$.
2) In TESS culture, media flow rate was 0.05 ml/min.
3) Two matricies from each group were harvested for histological analysis.

From the above description and examples, it should be clear that the present invention provides compositions and methods for the preparation of tissues and tissue constructs. Accordingly, this invention is not limited to the particular embodiments disclosed, but is intended to cover all modifications that are within the spirit and scope of the invention as defined by the appended claims.

We claim:

1. A method for preparation of an implantable tissue construct for treatment of a lesion of joint cartilage wherein said construct is implanted into a joint lesion of a human or non-human subject, said method comprising steps:
   a) isolating, culturing and expanding chondrocytes harvested from autologous or heterologous connective tissue;
   b) preparing an implantable multilayered construct comprising:
      (i) a first integration layer that is, upon implantation, contacted with a joint lesion in situ and prevents infiltration of blood vessels and cells from underlying bone tissue into an implanted cellular support layer,
   wherein said integration layer is comprised of an adhesive compound;
      (ii) a second cellular support layer comprising a matrix to be seeded with cultured and expanded chondrocytes of step a),
   wherein said matrix is a biodegradable honeycomb-like Type I collagen structure; and
      (iii) a third protective layer insulating the outer surface of the cellular support layer and protecting said support layer from mechanical or physiological trauma,
   wherein said protective layer comprises an adhesive compound applied to the cellular support layer before implantation of said cellular support layer or after placing the integration and cellular support layers into the joint or joint lesion;
   wherein said second cellular support layer is linked by adhesion to the first layer and the third protective layer is linked by adhesion to the second layer;
   c) seeding said chondrocytes of step a) into said matrix of the second cellular support layer of step b) (ii) wherein said chondrocytes are suspended in a sol-gel and contacted with said matrix;
   d) treating said seeded matrix of step c) before implantation into said join lesion with cyclic hydrostatic pressure in a range from about 0.01 to 10 MPa at 0.5 Hz for one to thirty days followed with a resting phase in the range of one to sixty days, wherein during said resting phase said seeded matrix is maintained at atmospheric pressure before implantation into the joint; and
   e) transplanting said three layers of the construct into the joint lesion.

2. The method of claim 1 wherein said chondrocytes are harvested from autologous or heterologous cartilage.

3. The method of claim 2 wherein said chondrocytes are seeded in said matrix by a capillary action or wicking.

4. The method of claim 3 wherein said chondrocytes are immobilized within said matrix to achieve an uniform distribution of chondrocytes.

5. The method of claim 1 wherein said first integration layer is further configured to protect said chondrocytes from the effect of blood-borne clotting factors, cytokines or cytotoxic cells.

6. The method of claim 1 wherein said cyclic hydrostatic pressure is in the range from 0.5 to 5 MPa at 0.5 Hz, the cyclic hydrostatic pressure treatment is administered for five to eight days and before implantation said treatment is followed by the resting phase in the range from four to twenty one days.

7. The method of claim 6 wherein said cyclic hydrostatic pressure is about 3 MPa at 0.5 Hz., wherein said cyclic hydrostatic pressure treatment is administered for about six days and wherein said resting phase is about twelve days.

8. The method of claim 7 wherein said treatment with the cyclic hydrostatic pressure results in increase in production of glycosaminoglycan by treated chondrocytes up to 300% compared to production of glycosaminoglycan at a static atmospheric pressure.

9. The method of claim 7 wherein said seeded matrix is treated with the cyclic hydrostatic pressure at 37° C. and at 5% $CO_2$.

10. The method of claim 9 wherein said seeded matrix is treated with the cyclic hydrostatic pressure at 37° C. at reduced oxygen concentration of less than 20% saturation.

11. The method of claim 10 wherein said oxygen concentration is between 0% and 19%.

12. The method of claim 11 wherein said oxygen concentration is about 2%.

13. The method of claim 1 wherein said adhesive compound is a polymer of polyethylene glycol and collagen, a co-collagen, fibrin, agarose, alginate, chitin, polylactic acid, polyglycolic acid or a co-polymer thereof.

14. The method of claim 1 wherein said honeycomb-like Type I collagen structure is prepared from Type I collagen by gelling an acidic aqueous solution of said Type I collagen with ammonia gas to form a collagen gel and freeze drying said gel into a porous dried matrix wherein sizes of pores are adjusted to a pore sizes in a range from about 100 to about 300 μm.

15. The method of claim 14 wherein the sizes of the pores are adjusted to a pore size of about 200 μm.

16. The method of claim 1 wherein said adhesive compound is polylactate or a co-polymer of polylactic and polyglycolic acid.

* * * * *